United States Patent
Danek et al.

(10) Patent No.: US 8,292,882 B2
(45) Date of Patent: *Oct. 23, 2012

(54) CONTROL METHODS AND DEVICES FOR ENERGY DELIVERY

(75) Inventors: Christopher J. Danek, San Carlos, CA (US); William J. Wizeman, Mountain View, CA (US); Tim R. Dalbec, Saratoga, CA (US); Gary S. Kaplan, Palo Alto, CA (US)

(73) Assignee: Asthmatx, Inc., Mountain View, CA (US)

( * ) Notice: Subject to any disclaimer, the term of this patent is extended or adjusted under 35 U.S.C. 154(b) by 1105 days.

This patent is subject to a terminal disclaimer.

(21) Appl. No.: 11/608,606

(22) Filed: Dec. 8, 2006

(65) Prior Publication Data
US 2007/0074719 A1  Apr. 5, 2007

Related U.S. Application Data

(63) Continuation of application No. 11/408,688, filed on Apr. 21, 2006.

(60) Provisional application No. 60/674,106, filed on Apr. 21, 2005.

(51) Int. Cl.
*A61B 18/12* (2006.01)

(52) U.S. Cl. ............................. 606/34; 606/32

(58) Field of Classification Search .................. 606/34, 606/37–40; 128/200.24; 600/549
See application file for complete search history.

(56) References Cited

U.S. PATENT DOCUMENTS

| | | | |
|---|---|---|---|
| 4,739,759 A | 4/1988 | Rexroth et al. | |
| 4,907,589 A | 3/1990 | Cosman | |
| 5,425,023 A | 6/1995 | Haraguchi et al. | |
| 5,496,312 A | 3/1996 | Klicek | |
| 5,540,681 A | 7/1996 | Strul et al. | |
| 5,562,503 A | 10/1996 | Ellman et al. | |
| 5,584,830 A * | 12/1996 | Ladd et al. ..................... | 606/34 |
| 5,688,267 A | 11/1997 | Panescu et al. | |
| 5,702,386 A | 12/1997 | Stern et al. | |
| 5,735,846 A | 4/1998 | Panescu et al. | |
| 5,782,827 A | 7/1998 | Gough et al. | |
| 5,837,001 A | 11/1998 | Mackey | |
| 5,931,835 A | 8/1999 | Mackey | |
| 5,954,686 A * | 9/1999 | Garito et al. ..................... | 604/37 |

(Continued)

FOREIGN PATENT DOCUMENTS

EP  908713 A1  4/1999

(Continued)

OTHER PUBLICATIONS

PCT International search report for application No. PCT/US06/15267 mailed on Mar. 14, 2007, 1 page.

*Primary Examiner* — Michael Peffley
*Assistant Examiner* — Samantha Good
(74) *Attorney, Agent, or Firm* — Bookoff McAndrews, PLLC

(57) ABSTRACT

Control systems and methods for delivery of energy that may include control algorithms that prevent energy delivery if a fault is detected and may provide energy delivery to produce a substantially constant temperature at a delivery site. In some embodiments, the control systems and methods may be used to control the delivery of energy, such as radiofrequency energy, to body tissue, such as lung tissue.

11 Claims, 5 Drawing Sheets

U.S. PATENT DOCUMENTS

| | | | |
|---|---|---|---|
| 5,957,961 A | 9/1999 | Maguire et al. | |
| 6,063,078 A | 5/2000 | Wittkampf | |
| 6,071,281 A | 6/2000 | Burnside et al. | |
| 6,092,528 A | 7/2000 | Edwards | |
| 6,123,702 A | 9/2000 | Swanson et al. | |
| 6,139,546 A * | 10/2000 | Koenig et al. | 606/34 |
| 6,179,785 B1 | 1/2001 | Martinosky et al. | |
| 6,183,468 B1 | 2/2001 | Swanson et al. | |
| 6,245,065 B1 | 6/2001 | Panescu et al. | |
| 6,264,653 B1 | 7/2001 | Falwell | |
| 6,346,104 B2 | 2/2002 | Daly et al. | |
| 6,355,031 B1 | 3/2002 | Edwards et al. | |
| 6,391,028 B1 * | 5/2002 | Fanton et al. | 606/45 |
| 6,458,121 B1 | 10/2002 | Rosenstock et al. | |
| 6,488,679 B1 | 12/2002 | Swanson et al. | |
| 6,494,880 B1 | 12/2002 | Swanson et al. | |
| 6,558,378 B2 | 5/2003 | Sherman et al. | |
| 6,575,969 B1 | 6/2003 | Rittman, III et al. | |
| 6,635,056 B2 | 10/2003 | Kadhiresan et al. | |
| 6,783,523 B2 | 8/2004 | Qin et al. | |
| 6,939,346 B2 | 9/2005 | Kannenberg et al. | |
| 7,104,987 B2 | 9/2006 | Biggs et al. | |
| 7,131,445 B2 | 11/2006 | Amoah | |
| 2001/0029315 A1 * | 10/2001 | Sakurai et al. | 600/101 |
| 2002/0198519 A1 * | 12/2002 | Qin et al. | 606/34 |
| 2003/0050631 A1 | 3/2003 | Mody et al. | |
| 2003/0069570 A1 | 4/2003 | Witzel et al. | |
| 2003/0187430 A1 | 10/2003 | Vorisek | |
| 2003/0225401 A1 * | 12/2003 | Eggers et al. | 606/39 |
| 2003/0233099 A1 * | 12/2003 | Danaek et al. | 606/96 |
| 2003/0236455 A1 | 12/2003 | Swanson et al. | |
| 2004/0010289 A1 * | 1/2004 | Biggs et al. | 607/2 |
| 2004/0030328 A1 * | 2/2004 | Eggers et al. | 606/34 |
| 2004/0092926 A1 * | 5/2004 | Hoey et al. | 606/34 |
| 2004/0097916 A1 * | 5/2004 | Thompson et al. | 606/34 |
| 2004/0153056 A1 | 8/2004 | Muller et al. | |
| 2005/0096644 A1 | 5/2005 | Hall et al. | |
| 2005/0193279 A1 | 9/2005 | Daners | |
| 2005/0251128 A1 | 11/2005 | Amoah | |
| 2006/0079887 A1 | 4/2006 | Buysse et al. | |
| 2006/0217700 A1 * | 9/2006 | Garito et al. | 606/34 |
| 2006/0247726 A1 | 11/2006 | Biggs et al. | |
| 2006/0247727 A1 | 11/2006 | Biggs et al. | |
| 2006/0247746 A1 | 11/2006 | Danek et al. | |
| 2009/0030477 A1 | 1/2009 | Jarrard | |

FOREIGN PATENT DOCUMENTS

| | | |
|---|---|---|
| JP | 59167707 A2 | 9/1984 |
| WO | WO-9903413 A1 | 1/1999 |

* cited by examiner

CONTROL METHODS AND DEVICES FOR ENERGY DELIVERY

CROSS-REFERENCE TO RELATED APPLICATIONS

This application is a continuation of and claims the benefit of priority of U.S. patent application Ser. No. 11/408,688, filed Apr. 21, 2006, which claims the benefit of priority of U.S. Provisional Patent Application Ser. No. 60/674,106, filed Apr. 21, 2005, the full disclosures of which are incorporated herein by reference.

BACKGROUND

Various obstructive airway diseases have some reversible component. Examples include COPD and asthma. Asthma is a disease in which bronchoconstriction excessive mucus production and inflammation and swelling of airways occur, causing widespread but variable airflow obstruction thereby making it difficult for the asthma sufferer to breathe. Asthma is a chronic disorder, primarily characterized by persistent airway inflammation. Asthma is further characterized by acute episodes of additional airway narrowing via contraction of hyper-responsive airway smooth muscle.

In susceptible individuals, asthma symptoms include recurrent episodes of shortness of breath (dyspnea), wheezing, chest tightness and cough. Currently, asthma is managed by a combination of stimulus avoidance and pharmacology. Stimulus avoidance is accomplished via systemic identification and minimization of contact with each type of stimuli. It may, however, be impractical and not always helpful to avoid all potential stimuli.

Pharmacological management of asthma includes long term control through the use of anti-inflammatories and long-acting bronchiodilators. Short term pharmacological management of acute exacerbations may be achieved with use of short-acting bronchiodilators. Both of these approaches require repeated and regular use of prescribed drugs. High doses of corticosteroid anti-inflammatory drugs can have serious side effects that require careful management. In addition, some patients are resistant to steroid treatment. The difficulty involved in patient compliance with phannacologic management and the difficulty of avoiding stimulus that trigger asthma are common barriers to successful conventional asthma management. Accordingly, it would be desirable to provide a management system and method that does not require regular patient compliance.

Various energy delivering systems have been developed to intraluminally treat anatomical structures by the controlled application of energy to intraluminal surfaces. Such systems may be specifically configured to deliver energy to lung tissue because of the clinical demands caused by the heterogeneous nature of lung tissue, and specifically, variations in lung tissue lumen size due to the branching pattern of the tracheobronchial tree, variations in the vasculature of the lungs and variations in the type of tissue in the lungs, including cartilage, airway smooth muscle, and mucus glands and ducts. Accordingly, a system designed to delivery energy, and in some particular cases, radiofrequency energy, to lung tissue must take these variations into account and deliver energy in a controlled manner.

Medical procedures involving the controlled delivery of therapeutic energy to patient tissue are often demanding and may require a physician to perform several tasks at the same time. In addition, medical procedures or other procedures may require specific energy delivery parameters. As such, what has been needed is an energy delivery system with a user friendly control system that regulates and controls the delivery of energy, prevents operation or energy delivery if a fault in the energy delivery system is detected by the control system and provides the user with information delivered in an easy to understand format so that the information can be readily analyzed during a demanding medical procedure.

SUMMARY

In one embodiment, a system for delivering activation energy to a therapeutic energy delivery device having a temperature detecting element and an energy emission element includes an energy generator configured to be coupled to the energy emission element. The energy generator has an activation state and a standby state, where activation energy is delivered to the energy emission device in the activation state and not in the standby state. A controller having a processor and a user interface surface with a visual indicator is coupled to the energy generator and the processor is configured to activate the visual indicator when a temperature measured by the temperature detecting element is not within a pre-determined temperature range.

In another embodiment, an energy delivery system includes a therapeutic energy delivery device having a distal portion configured to be delivered to a treatment site. The distal portion includes a temperature detecting element and an energy emission element. An energy generator is configured to be coupled to the energy emission element and has an activation state and a standby state, where activation energy is delivered to the energy emission element in the activation state and not in the standby state. A controller having a processor and a user interface surface with a visual indicator is configured to activate the visual indicator when a temperature measured by the temperature detecting element is not within a pre-determined temperature range.

In another embodiment, a system for delivering activation energy to a therapeutic energy delivery device having a temperature detecting element and an energy emission element includes an energy generator configured to be coupled to the energy emission element. The energy generator has an activation state and a standby state, where activation energy is delivered to the energy emission device in the activation state and not in the standby state. A controller having a processor and a user interface surface with a visual indicator is configured to activate the visual indicator when an impedance of an energy emission circuit between the energy generator, the energy emission element and a patient is not within a pre-detennined impedance range.

In another embodiment, an energy delivery system includes a therapeutic energy delivery device having a temperature detecting element and an energy emission element. An energy generator is configured to be coupled to the energy emission element and has an activation state and a standby state, where activation energy is delivered to the energy emission element in the activation state and not in the standby state. A controller having a processor and a user interface surface with a visual indicator is configured to activate the visual indicator when an impedance of an energy emission circuit between the energy generator, the energy emission element and a patient is not within a pre-determined. impedance range.

In yet another embodiment, a system for delivering activation energy to a therapeutic energy delivery device having a temperature detecting element and an energy emission element includes an energy generator configured to be coupled to the energy emission element. The energy generator has an activation state and a standby state, where activation energy is delivered to the energy emission device in the activation state and not in the standby state. A controller having a processor and a user interface surface with a first visual indicator and a second visual indicator, is configured to activate the first visual indicator when a temperature measured by the temperature detecting element is not within a pre-determined temperature range and to activate the second visual indicator when an impedance of an energy emission circuit between the energy generator, the energy emission element and a patient is not within a pre-determined impedance range.

In another embodiment, an energy delivery system includes a therapeutic energy delivery device configured to be delivered to a treatment site. The energy delivery device has a temperature detecting element and an energy emission element. An energy generator is configured to be coupled to the energy emission element and has an activation state and a standby state, where activation energy is delivered to the energy emission element in the activation state and not in the standby state. A controller having a processor and a user interface surface with a first visual indicator and a second visual indicator is configured to activate the first visual indicator when a temperature measured by the temperature detecting element is not within a predetermined temperature range and to activate the second visual indicator when an impedance of an energy emission circuit between the energy generator, the energy emission element and a patient is not within a pre-determined impedance range.

In another embodiment, an energy delivery system includes a therapeutic energy delivery catheter having an electrode and temperature detecting element disposed on a distal portion of the catheter. The distal portion of the catheter is configured to be delivered to a treatment site adjacent target tissue of a patient and deliver a treatment cycle of therapeutic RF energy to the target tissue. An RF energy generator is configured to be coupled to the electrode and has an activation state and a standby state, where RF energy is delivered to and emitted from the electrode in the activation state and not in the standby state. A controller having a processor and a user interface surface with a first visual indicator and second visual indicator is configured to process temperature measurements taken by the temperature detecting element and impedance measurements between the RF energy generator and the target tissue prior to activation of the RF energy generator to the activation state. The processor is also configured to activate the first visual indicator if a temperature measured by the temperature detecting element is not within a pre-determined temperature range and activate the second visual indicator when an impedance between the RF energy generator and target tissue adjacent the electrode is above a predetermined value.

These features of embodiments will become more apparent from the following detailed description when taken in conjunction with the accompanying exemplary drawings.

DETAILED DESCRIPTION

Embodiments of systems and methods for delivering energy to tissue of a patient in a controlled manner are discussed, and specifically, systems and methods for controlled delivery of radiofrequency (RF) energy to lung tissue, bronchial tissue or both. Embodiments of the systems and methods may be configured to consolidate and effectively communicate relevant information to a user of the systems, including detecting accessory connections (e.g. therapeutic device, footswitch, electrode return pad, or other) and serving as an automatic trouble shooting guide with user friendly instructions, information, indicators and the like.

Figure 1:
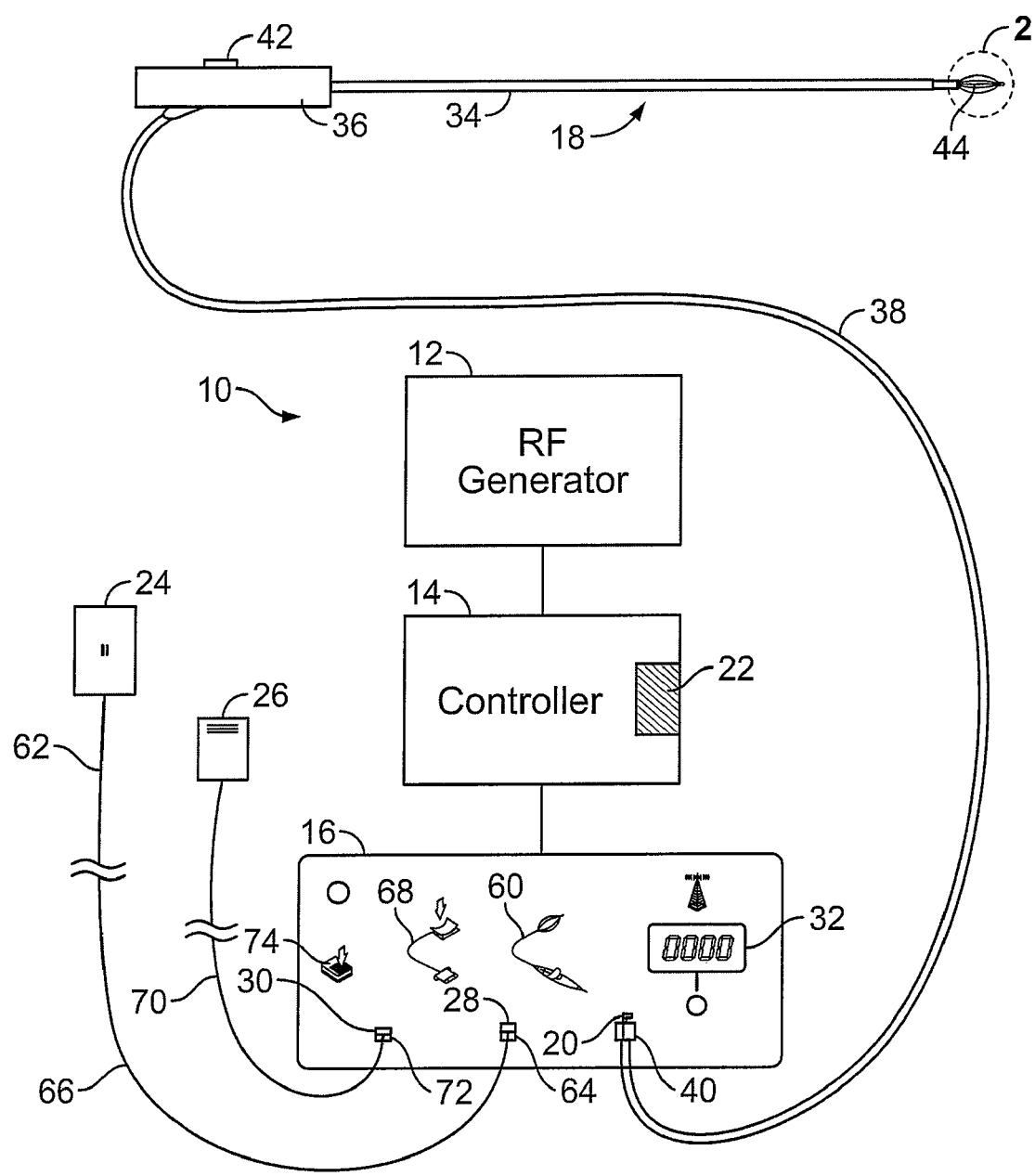
FIG. 1 is a schematic view of a system for delivering energy to the wall tissue of a patient's lung.
Figure 5A:
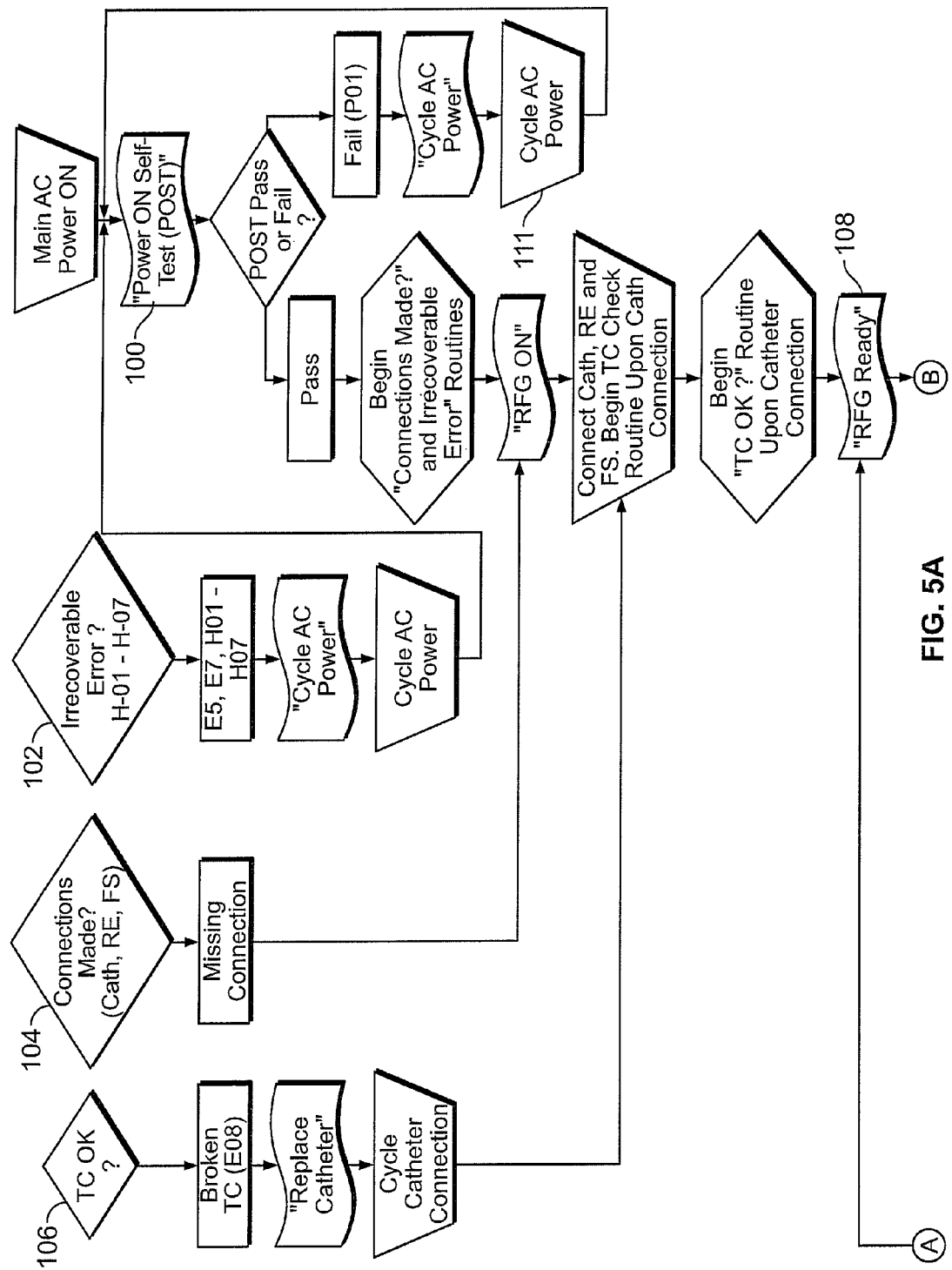
FIGS. 5A and 5B are flow diagrams depicting various processes and routines that control the user interface surface elements.
Figure 5B:
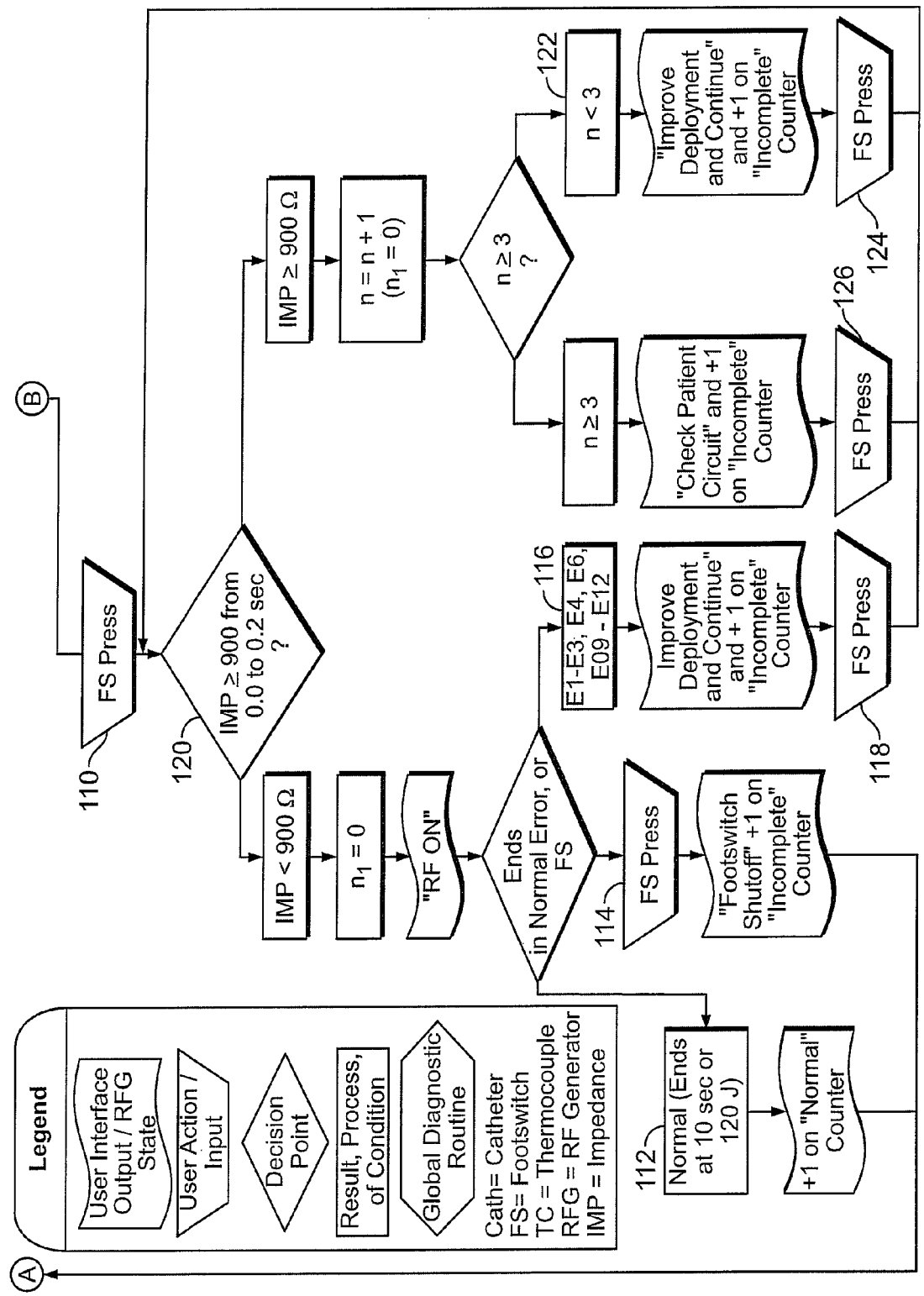

FIG. 1 shows a schematic diagram of a system for delivering therapeutic energy 10 to tissue of a patient having an RF energy generator 12, a controller 14 coupled to the energy generator, a user interface surface 16 in communication with the controller 14 and a therapeutic energy delivery device, in the form of an RF energy delivery catheter 18, coupled to an interface coupler 20 on the user interface surface 16. The controller 14, which is coupled to the energy generator 12 and user interface surface 16, is configured to control the energy output of the energy generator 12. The user interface surface 16 may include switches, a digital display, visual indicators, graphical representations of components of the system and an audio tone generator as well as other features. The controller 14 includes a processor 22 that is generally configured to accept information from the system and system components, and process the information according to various algorithms to produce control signals for controlling the energy generator 12. The processor 22 may also accept information from the system 10 and system components, process the information according to various algorithms and produce information signals that may be directed to the visual indicators, digital display or audio tone generator of the user interface in order to inform the user of the system status, component status, procedure status or any other useful information that is being monitored by the system. The processor 22 of the controller 14 may be digital IC processor, analog processor or any other suitable logic or control system that carries out the control algorithms. Some of the control alerts, information, feedback and testing routines are shown in the flow diagrams of FIGS. 5A and 5B.

The system 10 also includes an electrode return pad 24 and a footswitch 26, both of which are coupled to respective interface couplers 28 and 30 on the user interface surface 16. The user interface surface 16 also includes a digital display 32 that may be used to display numeric data to a user of the system 10. The arrangement of the user interface surface 16 provides a user friendly interface for the system 10 that provides feedback and system information to a user in an intuitive display format. System components that couple to the user interface surface 16, such as the footswitch 26, electrode return conductive pad 24 and energy delivery catheter 18, couple to the user interface surface 16 adjacent graphical representations of the respective system components. In addition, visual indicators that are configured to display information about these various system components may also be disposed adjacent or within the respective graphical representation of each system component. This configuration allows a user to easily and intuitively couple system components to the proper interface on the user interface surface 16 and also allows a user to easily and intuitively correlate audio and visual system feedback to the appropriate system component.

Referring again to FIG. 1, the energy delivery catheter 18 includes an elongate shaft 34, a handle 36 secured to a proximal end of the elongate shaft 34 and a control cable 38 that extends from the handle 36 to a proximal coupler 40 that is configured to couple to the interface coupler 20 on the user interface surface 16. A sliding actuator 42 on the handle 36 controls the radial expansion and contraction of a distal electrode basket 44 disposed on a distal end of the elongate shaft 34. The elongate shaft 34 may have a variety of configurations, including stiff, flexible, steerable with distal tip deflection and the like. The elongate shaft 34 and distal portion may also be configured and sized to permit passage of the elongate shaft 34 through the working lumen of a commercially available bronchoscope. In addition, the controller 14 may also include an optional interface coupler (not shown) that is configured to couple to a bronchoscope camera trigger such that when the processor 22 of the controller 14 initiates a treatment cycle by switching the RF energy generator from a standby state to an activation state, a triggering signal is also generated by the controller to initiate video taping or displaying of an image produced by the bronchoscope camera which is coupled to a bronchoscope being used to position the energy delivery catheter 18 during a procedure or treatment cycle. Alternatively, an interface couple may provide the ability to send some or all of the controller output or feedback to the bronchoscope video processor or monitor. This feature allows display of information ordinarily on the controller's user interface surface to display on any of the bronchoscope video monitors. Additionally, additional controller output information that is not displayed on the controller's user interface surface can be displayed on any of the displays associated with the bronchoscope. This feature allow the the physician to focus on the bronchoscope display monitor when performing a procedure.

Figure 2:
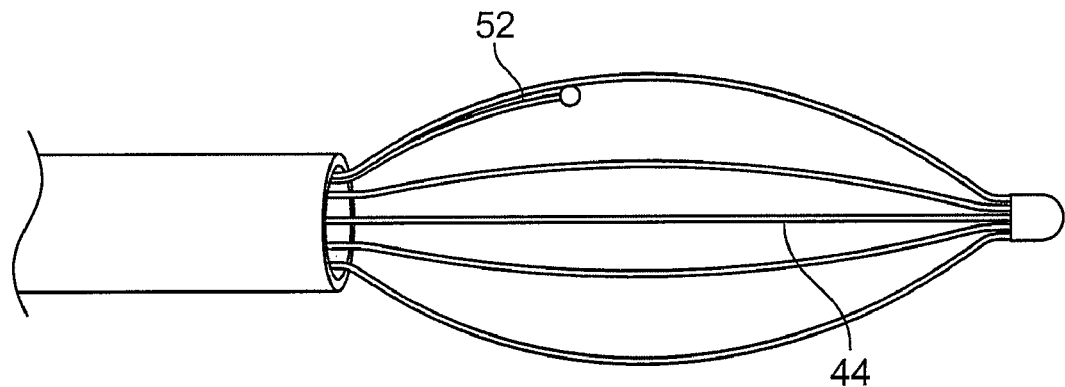
FIG. 2 is an enlarged view of a distal portion of a therapeutic energy delivery device.
Figure 3:
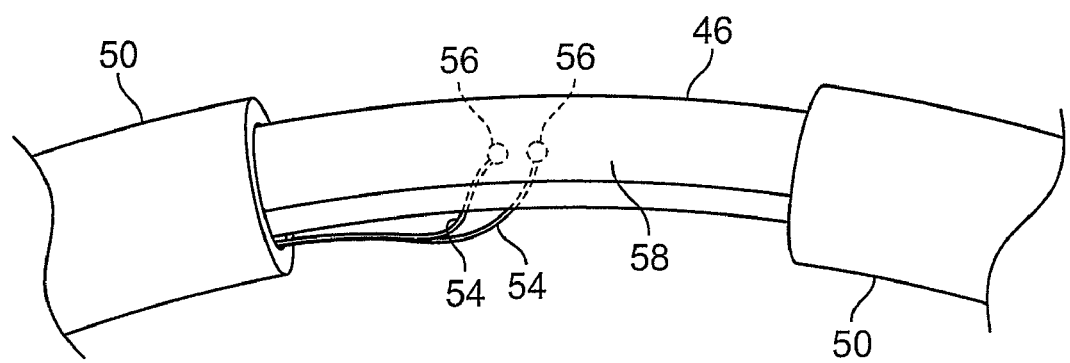
FIG. 3 is an enlarged view of a portion of FIG. 2 illustrating a more detailed view of an energy emission element and temperature detecting element of the therapeutic energy delivery device.

The distal electrode basket 44 may be seen in more detail in FIGS. 2 and 3. The distal electrode basket 44 is a flexible and resilient oval shaped basket that includes an energy emission element in the form of an electrode 46 that is formed from an exposed section of a basket leg 58 which is nominally coated with an electrical insulator material 50 in the areas outside of the exposed section. The distal electrode basket 44 also includes a temperature detection element in the form of a thermocouple 52 disposed on or adjacent the electrode 46. The thermocouple 52 has leads 54 and thermocouple termination points 56 which are secured to the exposed section 58 of the basket leg or electrode 46.

The leads 54 of the thermocouple 52 and a conductor (not shown) in electrical communication with the electrode 46 extend proximally from the distal basket 44 to the handle 36 and then proximally through the control cable 38 to the proximal coupler 40. This configuration allows the electrode 46 and the thermocouple leads 54 to be electrically coupled in a modular arrangement with the controller 14 through the user interface surface 16. The interface coupler 20 configured to accept the proximal coupler 40 of the energy delivery catheter 18 is disposed adjacent a graphical representation 60 of an embodiment of the energy delivery catheter 18 which is printed on the user interface surface 16. This provides a useful visual prompt for a user who is setting up the system 10. Once the proximal coupler 40 is connected to the interface coupler 20 for the energy delivery catheter 18, the electrode 46 is now in electrical communication with the RF energy generator 12, subject to control and modulation by the controller 14 which may switch the RF generator 12 back and forth between an active state and a standby state, during which no RF can be delivered. In addition, the leads 54 of the thermocouple 52 are also in electrical communication with the controller 14 so that the controller 14 may monitor the temperature of the tissue adjacent the electrode 46. In this arrangement, the RF energy generator 12, controller 14 and user interface 16 form a system for controlled delivery of activation energy to the energy delivery catheter 18.

The electrode 46 may be monopolar or bipolar, however, if the electrode 46 is a monopolar electrode, a return electrode component 62 may be used with the system 10 in order to complete an electrical energy emission or patient circuit between the RF energy generator 12 and a patient (not shown). The electrode return 62 includes the conductive pad 24, a proximal coupler 64 and a conductive cable 66 extending between and in electrical communication with the conductive pad 24 and proximal coupler 64. The conductive pad 24 may have a conductive adhesive surface configured to removably stick to the skin of a patient and with a large enough surface area such that no burning or other injury to the patient's skin will occur in the vicinity of the conductive pad 24 while the system 10 is in use. The proximal coupler 64 is configured to couple to the interface coupler 28 on the user interface surface 16. The interface coupler 28 for the electrode return 62 is disposed adjacent a graphical representation 68 of the electrode return 62 on the user interface surface 16. Once again, this provides a useful visual prompt for a user who is setting up the system 10.

Once the proximal coupler 40 of the energy delivery catheter 18 and the proximal coupler 64 of the electrode return 62 have been coupled to the controller 14 via the respective interface couplers 20 and 28 of the user interface surface 16, RF energy may be generated by the RF generator 12, i.e., the RF generator 12 is switched to an activation state, and emitted from the electrode 46 of the distal basket 44 of the energy delivery catheter 18 into target tissue of the patient adjacent the electrode 46. The processor 22 may then adjust the output of the RF generator 12 in order to maintain a substantially constant temperature of tissue adjacent the electrode via a feedback loop between the thermocouple 52 and the processor 22. The processor 22 may use a control algorithm to process the temperature feedback and generate control signals for the RF generator 12. In addition, the control algorithm may be configured to set predetermined dwell or activation times for embodiments of treatment cycles. Embodiments of control algorithms and system components that may be used in conjunction with control device and method embodiments discussed herein may be found in U.S. patent application Ser. No. 10/414,411, titled "Control System and Process for Application of Energy to Airway Walls and Other Mediums", filed Apr. 14, 2003, which is incorporated by reference herein in its entirety.

Additionally, devices and methods for treating airway wall are described in U.S. patent application Ser. No. 09/095,32 entitled METHOD AND APPARATUS FOR TREATING SMOOTH MUSCLES IN THE WALLS OF BODY CONDUITS filed Jun. 10, 1998; Ser. No. 10/414,253 titled MODIFICATION OF AIRWAYS BY APPLICATION OF ENERGY filed Apr. 14, 2003; Ser. No. 09/436,455 titled DEVICES FOR MODIFICATION OF AIRWAYS BY TRANSFER OF ENERGY filed Nov. 8, 1999; Ser. No. 09/999,851 titled METHOD FOR TREATING AN ASTHMA ATTACK filed Oct. 25, 2001; Ser. No. 10/810,276 titled METHOD OF TREATING AIRWAYS IN THE LUNG filed Mar. 26, 2004; Ser. No. 10/640,967 titled METHODS OF TREATING ASTHMA filed Aug. 13, 2003; Ser. No. 10/809,991 titled METHODS OF TREATING REVERSIBLE OBSTRUCTIVE PULMONARY DISEASE filed Mar.

26, 2004; and Ser. No. 10/954,895 titled INACTIVATION OF SMOOTH MUSCLE TISSUE filed Sep. 30, 2004; and U.S. Pat. No. 6,411,852 titled CONTROL SYSTEM AND PROCESS FOR APPLICATION OF ENERGY TO AIRWAY WALLS AND OTHER MEDIUMS; and U.S. Pat. No. 6,634,363 titled DEVICES FOR MODIFICATION OF AIRWAYS BY TRANSFER OF ENERGY. Each of which of the above are incorporated by reference herein in their entirety In one embodiment, the RF generator 12 generates RF energy at a frequency of about 400 kHz to about 500 kHz in with a wattage output sufficient to maintain a target tissue temperature of about 60 degrees C. to about 80 degrees C., specifically, about 60 degrees C. to about 70 degrees C. The duration of the activation state for an embodiment of a single treatment cycle may be about 5 seconds to about 15 seconds, specifically, about 8 seconds to about 12 seconds. Alternatively, the duration of the activation state of the RF generator may also be set to not more than the duration required to deliver about 150 Joules of energy to the target tissue, specifically, not more than the duration required to deliver about 125 Joules of RF energy to target tissue.

The initiation of the activation state of the RF generator 12 may be carried out by a variety of devices and methods, however, the embodiment of FIG. 1 includes a user operated activation switch in the form the footswitch 26. A conductive cable 70 is coupled to and disposed between the footswitch 26 and a proximal coupler 72 which is configured to be electrically coupled to the respective interface coupler 30 disposed on the user interface surface 16. The interface coupler 30 for the proximal coupler 72 of the footswitch 26 is disposed adjacent a graphical representation 74 of the footswitch 26 on the user interface surface 16. The footswitch 26 may be used in some configurations to initiate an activation state of the RF energy generator 12 if all components of the system 10 are functioning and connected properly. This can be defined as the controller entering into the ready mode.

Figure 4:
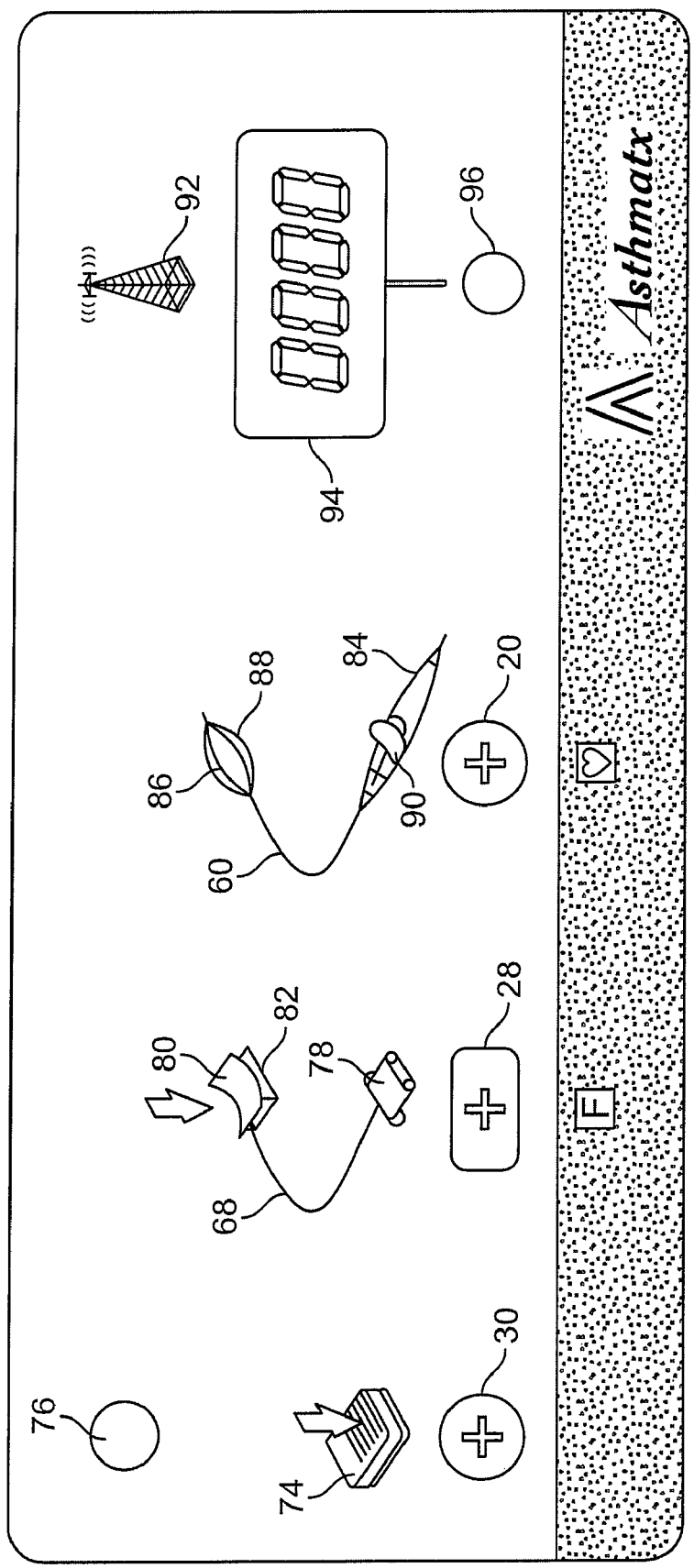
FIG. 4 is an elevational view of a user interface surface of a controller.

Referring now to FIG. 4, a more detailed view of an embodiment of the user interface surface 16 is shown. The user interface surface 16 may be a substantially rectangular and flat surface as shown in FIG. 4, but may also have any other suitable shape, size or configuration. The user interface surface 16 may, in some embodiments, be any part of an energy delivery system, or component thereof, that a user may access or see in order to impart information or receive information therefrom. The controller 14 may have an alternating current (AC) power on/off switch that may be located anywhere on the controller 14, or alternatively, on the user interface surface 16. However, for the embodiment shown in FIG. 4, the user interface surface 16 does not include an AC power on/off switch. The controller 14 or user interface surface 16 may include an audio tone generator (not shown) which may be used in conjunction with the various visual indicators of the system 10 to alert a user to the status of the various components of the system 10. In one embodiment, the audio tone generator includes a speaker (not shown) which may be mounted on any suitable surface of the controller 12 or the user interface surface 16.

The user interface surface 16 has a visual indicator in the form of a multi-colored LED (light emitting diode) ready indicator light 76 in the upper left hand corner of the user interface surface 16. The ready indicator light 76 may be activated or lit with a first color, such as a green color, when the RF energy generator 12 is ready for use in a standby state. The LED indicator 76, may be activated and lit with a second color, such as an amber color, when the RF energy generator 12 is switched on into an activation state at which time a brief audio tone may also sound upon the transition of the RF generator 12 from the standby or ready state to the activation state with RF energy being delivered to the energy emission element 46 of the energy delivery catheter 18. Additionally, a separate LED indicator 92 may be activated and lit with a second color, such as a blue color, during RF energy delivery. Typically, a user activates the RF energy generator 12 for a treatment cycle by depressing and releasing the footswitch 26. The color of the ready indicator light 76 may be switched back to the first color if, during an activation cycle, the footswitch 26 of the system 10 is depressed and released again so as to produce a footswitch shutoff response from the processor 22 which switches the RF energy generator 12 from the activation state to the standby state. The second color or amber color may also be displayed by the ready indicator light 76 when the system 10 is engaged in a power on self-test (POST) mode during which time the audio tone generator may be delivering a constant single pitch tone. In addition, the second amber color may also be displayed by the ready indicator when a fault with the energy delivery catheter 18, such as a broken electrode 46 or broken thermocouple 52, is detected by the controller 14. The activation of the second color indicating a fault with the energy delivery catheter 18 may also be accompanied by an audible first error tone from the audio tone generator. The ready indicator light 76 may flash the first color, green, when the system 10 is conducting a cycling of the AC power to the controller 14 in order to reset the system 10 during which time the audible first error tone may also be produced. In essence, the ready indicator light 76 emits a first color when the system 10 is ready to use and a second color or amber color if the system 10 has detected a fault in the system 10 and is not ready to use.

Below the LED ready indicator 76 is the graphical representation 74 of the footswitch 26 which is printed on the user interface surface 16. The graphical representation 74 of the footswitch 26 is directly above and adjacent to the interface coupler 30 which is configured to accept the proximal coupler 72 of the footswitch 26 assembly. The graphical representation 74 of the footswitch 26 adjacent the interface coupler 30 for the footswitch 26 provides an intuitive and user friendly prompt for the user to locate the plug in point for the footswitch 26 while setting up the system 10.

To the right of the graphical representation 74 of the footswitch 26 is the graphical representation 68 of the electrode return assembly 62 which includes the conductive pad 24, conductive cable 66 and proximal coupler 64 and which is printed on the user interface surface 16. The graphical representation 78 of the proximal coupler 64 of the electrode return assembly 62 is disposed directly above and adjacent to the interface coupler 28 for the proximal coupler 64 of the electrode return assembly 62. A visual indicator in the form of an amber colored LED light 80 is disposed within the graphical representation 82 of the conductive pad 24 of the electrode return assembly 62 and on the user interface surface 16. The visual indicator 80 may be configured to be lighted in a steady state when the system 10 is proceeding through the POST which may also be accompanied by a single pitch audible tone from the audio tone generator. The visual indicator 80 may also be activated and lighted when the controller 14 measures an impedance in the patient circuit that is above a predetermined value after 3 or more attempts to activate the RF energy generator to the activation state. A second error tone may accompany the activation of the visual indicator in this circumstance. For some embodiments, the predetermined impedance value for the patient circuit may be above about 1000 Ohms, specifically, above about 900 Ohms. Such a high impedance measurement in the patient circuit indicates an open circuit and requires that the user check the patient circuit and try the system 10 another time. The patient circuit includes the electrode 46 and conductive cable 38 of the energy delivery catheter 18, the patient (not shown) with the conductive pad 24 and electrode 46 in electrical communication with the patient's body, and the electrode return assembly 62, The visual indicator 80 may also be activated or lighted in a flashing mode when a fault requiring the user to cycle AC power has been initiated by the processor 22, during which time a first audible error tone may also be generated by the audio tone generator.

To the right of the graphical representation 68 of the electrode return 62, the graphical representation 60 of the energy delivery catheter 18 is printed on the user interface surface 16 including the handle 36, the elongate shaft 34 and the distal electrode basket 44. The interface coupler 20 configured to accept the proximal coupler 40 of the energy delivery catheter 18 is disposed adjacent and directly below a graphical representation 84 of the handle 36 of the energy delivery catheter 18. A first visual indicator in the form of an amber LED light 86 is disposed within the graphical representation 88 of the distal electrode basket 44 on the user interface surface 16. A second visual indicator 90, having a second color different from the first visual indicator, in the form of a red LED light 90 is disposed within the graphical representation 84 of the handle 36.

The first visual indicator 86 may be activated and lighted for some embodiments of the system 10 when the controller 14 measures an impedance in the patient circuit that is above a predetermined value. For some embodiments, the predetermined impedance value for the patient circuit may be above about 1000 Ohms, specifically, above about 900 Ohms. A first audible error tone may also be generated during such an activation. The first visual indicator 86 may also be lighted or activated when the measured impedance of the patient circuit is above such a predetermined value during at least 3 or more attempts to activate the RF energy generator 12 to the activation state. In this circumstance, a second audible error tone may also be generated in conjunction with the activation of the first visual indicator 86. The first visual indicator 86 may also be lighted in a steady state when the processor 22 of the system 10 is proceeding through the POST which may also be accompanied by a single pitch audible tone from the audio tone generator. The visual indicator 86 may also be activated or lighted in a flashing mode when a fault requiring the user to cycle AC power has been initiated by the processor 22, during which time a first audible error tone may also be generated by the audio tone generator.

The second visual indicator 90 may be activated or lighted in a flashing or intermittent mode when a fault with the energy delivery catheter 18, such as a broken electrode 46 or broken thermocouple 52, is detected by the controller 14. The activation of the second visual indicator 90 suggesting a fault with the energy delivery catheter 18 may also be accompanied by an audible first error tone from the audio tone generator. The second visual indicator 90 may also be lighted in a steady state when the processor 22 of the system 10 is proceeding through the POST which may also be accompanied by a single pitch audible tone from the audio tone generator. The second visual indicator 90 may also be activated or lighted in a flashing mode when a fault requiring the user to cycle AC power has been initiated by the processor 22, during which time a first audible error tone may also be generated by the audio tone generator.

Another visual indicator 92 in the form of a graphical representation of a radiating electrode is disposed on the user interface surface 16. This RF energy indicator 92, which may be a third color or blue LED, is activated or lighted in a flashing mode during the time when the RF energy generator 12 is switched to the activation state and delivering RF energy to the energy delivery catheter 18. The RF energy indicator 92 may also be lighted in a steady state when the processor 22 of the system 10 is proceeding through the POST which may also be accompanied by a single pitch audible tone from the audio tone generator. The RF energy indicator 92 may also be activated or lighted in a flashing mode when a fault requiring the user to cycle AC power has been initiated by the processor 22, during which time a first audible error tone may also be generated by the audio tone generator.

A digital display 94 is disposed on the user interface surface 16 below the RF energy indicator 92 and is configured to display numerical information. The digital display 94 may be controlled or otherwise reset by a switch 96 disposed directly below the digital display 94 on the user interface surface 16. In a normal mode, the digital display 94 will display the number of successful treatment cycles delivered by the system 10 performed by a user of the system 10. If the switch 96 is depressed for less than about 2 seconds to about 4 seconds, the number of unsuccessful or incomplete treatment cycles is displayed for a brief period, such as about 5 seconds. After this brief period, the digital display 94 reverts back to a display of the number of completed treatment cycles. When the switch 96 is depressed and held for more than a brief period of about 2 seconds to about 4 seconds, the digital display 94 shows a "0" for a short period, such as about 1 second. If the switch 96 is held depressed during this short 1 second period, the count of the complete and incomplete treatment cycles is reset to 0. If the switch 96 is released during this short 1 second period, the digital display 94 reverts back to a display of the completed or successful treatment cycles without resetting the treatment cycle counter.

Referring to FIG. 5, a variety of system process embodiments are shown in flow diagram form. In use, the system 10 for delivery of therapeutic energy is first supplied with power, such as AC power, which may be carried out by a switch (not shown) on the controller 14 or user interface surface 16, as discussed above. Once AC power is supplied to the controller 14, the processor 22 initiates the POST cycle, indicated by box 100, which tests the integrity of the processor 22, the controller 14 and the system 10 generally. If the POST fails, the user initiates a cycling of the AC power in order to reboot the controller 14, and specifically, the processor 22 of the controller 14. In addition, once AC power has been supplied to the controller 14, the processor 22 continually runs a first background algorithm, indicated by the decision point "irrecoverable error" 102. The irrecoverable error test checks for hardware and processor errors such as CPU configuration, COP timeout, ROM CRC error, RAM, illegal CPU instruction, software, non-volatile memory, RF current measurement errors. If such an error is detected, the user should initiate a cycling of the AC power, as indicated by box 111, in order to reboot the controller 14, and specifically, the processor 22 of the controller 14. During the cycling of the AC power, the user will be informed of the cycling status by a flashing of all visual indicators on the user interface surface 16 as well as a flashing of the digital display 94 and the concurrent generation of an audible error tone.

If the POST is successful, the processor 22 will initiate a test algorithm that determines whether all connections of system components, such as the energy delivery catheter 18, return electrode 62 and footswitch 26 are all properly coupled to the respective interface couplers 20, 28 and 30 of the user interface surface 16, as indicated by decision point 104. If an error is detected during this routine, the ready indicator light 76 will remain in the second or amber color state, indicating that the RF energy generator 12 is not ready or in the standby state. Once the system components such as the energy delivery catheter 18, electrode return 62 and footswitch 26 are properly coupled to the user interface 16, the processor 22 will initiate an algorithm that determines whether the temperature detection element, or thermocouple 52, of the energy delivery catheter 18 is properly functioning as indicated by box 106.

During this test, the processor 22 measures the temperature indicated by the thermocouple 52 and compares the result to a predetermined temperature range, that encompasses room temperature for some embodiments. For example, the predetermined temperature range for some embodiments may be about 15 degrees C. to about 35 degrees C., specifically, about 20 degrees C. to about 30 degrees C. If the measured temperature indicated by the thermocouple 52 does not fall within the predetermined temperature range, the processor 22 indicates a broken thermocouple 52 by initiating an error message to the user which includes switching the ready indicator light 76 to the second or amber color in addition to initiating a flashing mode activation of the red LED second visual indicator 90 in the handle 84 of the graphical representation 60 of the energy delivery catheter 18. An audible error tone may also accompany the error message generated by the visual indicators 76 and 90. These error messages inform the user that it may be necessary to replace the energy delivery catheter 18 with a new one.

Once the thermocouple test has been successfully performed, the processor 22 will switch the ready indicator light 76 to the first color or green color indicating that the system 10 is now ready to perform a treatment cycle in a patient, as indicated by box 108. At this point, the user may then position the distal electrode basket 44 of the energy delivery catheter 18 such that at least one emission element or electrode 46 is disposed adjacent target tissue of the patient, such as smooth muscle of the patient's bronchial airways. Once the electrode 46 is properly positioned, the user depresses the footswitch 26 to initiate a treatment cycle, as indicated by user action/input box 110. Upon depression of the footswitch 26, the processor 22 immediately measures the impedance of the patient circuit, and if the impedance is below a predetermined maximum or within a predetermined impedance range, the processor 22 switches the RF energy generator 12 from the ready or standby state to the activation state wherein RF energy is being delivered to the target tissue of the patient for the initiation of a treatment cycle.

For some embodiments of a normal treatment cycle, as indicated by result box 112, the processor 22 and algorithms run by the processor 22 are configured to maintain the RF energy generator 12 in the activation state for a dwell time of about 5 seconds to about 15 seconds, specifically, about 8 seconds to about 12 seconds. The duration of the treatment cycle may also be constrained by the total energy delivered to the target tissue during the cycle. For example, the processor 22 may execute an algorithm which terminates the treatment cycle when the total energy delivered to the target tissue is up to about 150 Joules, specifically, up to about 125 Joules. During the treatment cycle, the processor 22 controls the output of the RF energy generator 12 in order to maintain a substantially constant temperature of the target tissue. The temperature of the target tissue during a treatment cycle embodiment may be maintained at a temperature of about 60 degrees C. to about 80 degrees C., specifically, from about 60 degrees C. to about 70 degrees C. As discussed above, the processor 22 is able to maintain the substantially constant temperature of the target tissue by monitoring the temperature of the target tissue via the temperature measuring element or thermocouple 52 and processing the temperature information in a feedback loop which lowers the RF energy generator 12 output if the measured temperature is higher than desired and increases the RF energy generator output if the measured temperature is lower than desired.

During the treatment cycle, the processor 22 will switch the blue RF energy visual indicator 92 to an activated solid or flashing mode and will activate the audio signal generator to generate a dual pitch audible tone from the audible tone generator that repeats a high pitch then low pitch audible tone during the treatment cycle, followed by a long single pitch tone at the end of a successful cycle. If an error occurs in the middle of a treatment cycle, an audible error tone will be generated and the visual indicator or indicators indicative of the error will be activated as discussed above. As discussed above, a treatment cycle may also be interrupted by the user's depression of the footswitch 26 during the treatment cycle to initiate a footswitch shutoff, as indicated by user action box 114. This may be done if the user feels that the system 10 is operating improperly for any reason, the user feels that the location of the electrode 46 is wrong, or for any other reason. A footswitch shutoff action by the user returns the system 10 to the RF generator ready state, indicated by box 108, but does not log a completed or successful treatment cycle on the digital display 94. If the treatment cycle is successfully completed, the digital display 94 will display a count of "1", indicating one successfully completed treatment cycle.

If an error occurs during the treatment cycle, as indicated by result box 116, or the footswitch shutoff option is used, a "0" will remain displayed. However, if the display control switch 96 is depressed for more than about 2 seconds to about 4 seconds, the digital display 94 will show a "1", indicating one incomplete or unsuccessful treatment cycle. The user may continue to deploy the energy delivery catheter 18 to new locations within the patient's anatomy and activate the RF energy generator 12 to the activation state for any desired number of treatment cycles. If an error occurs during a treatment cycle, as indicated by result box 116, the user interface 16 will then display via the appropriate visual indicators and audible tone indicators, the type of error that has occurred and will recommend a course of action for the user. After correction has been attempted by the user, the footswitch 26 may again be depressed, as indicated by user action/input box 118, in order to initiate another treatment cycle.

If the impedance of the patient circuit is greater than a predetermined maximum or not within a predetermined impedance range upon depression of the footswitch 26, as indicated by result box 120, one of two error messages including visual indicators and audible tones may be generated by the system 10. Specifically, if a high impedance is measured upon a first depression of the footswitch 26 or a second depression of the footswitch 26, as indicated by box 122, the error message "improve deployment and continue" will be generated, as discussed above, whereby the amber visual indicator 86 of the distal basket graphic 88 on the user interface 16 will be activated and lighted and a first error tone will be generated by the audible tone generator. In addition, an incomplete treatment cycle will be logged by the digital display 94. Once attempted correction has been made, the footswitch 26 may again be depressed as indicated by user action/input box 124, in which case the treatment cycle is reinitiated.

If on the third or subsequent depression of the footswitch 26 the same error is detected by the system 10, the "check patient circuit" error message will be generated, as discussed above, whereby the amber visual indicator 80 of the return electrode graphic 82 and the amber visual indicator 86 of the electrode basket graphic 88 on the user interface surface 16 will be activated and lighted. Such an error message may also be accompanied by a second audible error tone generated by the audible tone generator. In addition, an incomplete treatment cycle will be logged by the digital display 94. After attempted correction of the error, the footswitch 26 may again be depressed, as indicated by user action/input box 126, in order to initiate another treatment cycle.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A method for delivering activation energy to an airway in a lung with a treatment device having an energy generator, a temperature sensor mounted on the treatment device, a controller coupled to the energy generator, and an energy delivering element, the method comprising: providing a user interface having an energy delivery element indicator configured to represent at least a portion of the energy delivery element; sensing an ambient temperature with the temperature sensor mounted on the treatment device before inserting an electrode of the energy delivery element into a patient, wherein the controller causes the energy delivery element indicator to emit a first light indicating that the energy delivery element is not operable and should be replaced when the sensed ambient temperature is not within a range; positioning the energy delivery element in the lung of the patient; activating a switch that initiates delivery of energy to airway tissue in the lung via the energy delivery element; sensing temperature of the airway tissue with the temperature sensor mounted on the treatment device; sensing impedance via the energy delivery element and a return electrode attached to the patient; and wherein the controller causes the energy delivery element indicator to emit a second light when the impedance is above a predetermined impedance level indicating that the energy delivery element should be redeployed.

2. The method of claim 1, wherein the user interface further includes a system ready indicator configured to emit a first color indicating a ready state and a second color indicating a standby state, and the method further comprises precluding activation of the energy generator when the system ready indicator is emitting the second color.

3. The method of claim 2, further comprising activating an audible signal generator simultaneously when the system ready indicator changes from the first color to the second color.

4. The method of claim 1, wherein the pre-determined impedance is at least about 900 Ohms.

5. The method of claim 1, wherein the range is 15° C. to 30° C.

6. The method of claim 1, wherein the range is 20° C. to 30° C.

7. The method of claim 1, further comprising activating an audible signal generator when the energy generator exits a standby state and enters an activation state.

8. The method of claim 7, wherein changing the energy generator from the standby state to the activation state initiates a treatment cycle.

9. The method of claim 8, further comprising displaying a number of completed or uncompleted treatment cycles on the user interface.

10. The method of claim 1, wherein the user interface comprises a bronchoscope monitor or a controller interface.

11. The method of claim 1, wherein the user interface includes a system ready indicator configured to emit a first color indicating a ready state and a second color indicating a standby state, and the energy delivery element indicator comprises a first component configured to emit the first light and a second component configured to emit the second light separately and independently from the first light, and the method further comprises: detecting whether the energy delivery element is electrically coupled to the user interface, wherein the controller causes the system ready indicator to emit the first color when the energy delivery element is connected to the user interface and the second color when the energy delivery element is not connected to the user interface.

* * * * *